United States Patent [19]

Hirai et al.

[11] Patent Number: 4,603,103

[45] Date of Patent: Jul. 29, 1986

[54] HEAT-DEVELOPABLE LIGHT-SENSITIVE MATERIALS

[75] Inventors: Hiroyuki Hirai; Kozo Sato; Hiroshi Hara, all of Kanagawa, Japan

[73] Assignee: Fuji Photo Film Co., Ltd., Kanagawa, Japan

[21] Appl. No.: 675,040

[22] Filed: Nov. 26, 1984

[30] Foreign Application Priority Data

Nov. 25, 1983 [JP] Japan .............................. 58-221535
Apr. 5, 1984 [JP] Japan ................................ 59-68052

[51] Int. Cl.$^4$ .............................................. G03C 1/02
[52] U.S. Cl. ................................... 430/559; 430/562; 430/567; 430/568; 430/620; 430/617; 430/618; 430/619; 430/958
[58] Field of Search ............... 430/617, 618, 619, 620, 430/559, 567, 568, 958, 562

[56] References Cited

U.S. PATENT DOCUMENTS

| 4,207,112 | 6/1980 | Ikenoue et al. | 430/617 |
| 4,258,129 | 3/1981 | Ikenoue et al. | 430/620 |
| 4,259,424 | 3/1981 | Endo et al. | 430/617 |
| 4,500,626 | 2/1985 | Naito et al. | 430/619 |

FOREIGN PATENT DOCUMENTS 54-41887 12/1979 Japan ................................... 430/617

*Primary Examiner*—Won H. Louie
*Attorney, Agent, or Firm*—Sughrue, Mion, Zinn, Macpeak & Seas

[57] ABSTRACT

A heat-developable light-sensitive material comprising, on a support, a thermally decomposable organic silver salt. The heat-developable light-sensitive materials have high density and low fog.

16 Claims, No Drawings

HEAT-DEVELOPABLE LIGHT-SENSITIVE MATERIALS

FIELD OF THE INVENTION

The present invention relates to heat-developable light-sensitive materials containing a thermally decomposable organic silver salt.

BACKGROUND OF THE INVENTION

Some of the silver halides used for heat-developable light-sensitive materials contain silver iodide crystals in the grain thereof and, therefore, they can be used without using organic silver salts, such as silver chloroiodide, silver iodobromide or silver chloroiodobromide. In such silver halides, the X-ray pattern of silver iodide crystals appears. However, it is advantageous to use silver halides together with organic silver salts, because all of the silver halides known in this art can be used and a higher maximum density can be obtained.

Typical examples of such organic silver salts include silver salts of aliphatic carboxylic acids and silver salts of aromatic carboxylic acids.

Further, there are silver salts of aliphatic carboxylic acids having a thioether group as described in U.S. Pat. No. 3,330,663.

However, these silver salts of carboxylic acids are disadvantageous in that they release acids after reacting with a reducing agent to reduce the pH in the film and thus subsequent development is restrained.

Organic silver salts other than carboxylic acids include silver salts of compounds having a mercapto group or a thione group and derivatives thereof.

In addition, there are silver salts of compounds having an imino group such as silver salts of benzotriazole or derivatives thereof, etc., as described in Japanese Patent Publication Nos. 30270/69 and 18416/70.

However, these silver salts are disadvantageous in that they release a compound which restrains development or, in some cases, causes fog after reacting with a reducing agent. In addition, they sometimes inhibit the functions of spectral sensitizing dyes, and high sensitivity cannot be obtained.

SUMMARY OF THE INVENTION

An object of the present invention is to provide light-sensitive materials whereby images having high density are obtained in a short time.

A second object of the present invention is to provide light-sensitive materials whereby images having high density and low fog are obtained.

A third object of the present invention is to provide organic silver salts for heat-developable light-sensitive materials which do not show any adverse side-effect after heat-development.

A fourth object of the present invention is to provide light-sensitive materials whereby color images having high density and low fog are obtained.

The above described objects are attained by heat-developable light-sensitive materials comprising, on a support, a thermally decomposable organic silver salt.

DETAILED DESCRIPTION OF THE INVENTION

Of the above described thermally decomposable organic silver salts, preferred examples thereof which can be employed in the present invention are silver salts of carboxylic acids which undergo decarboxylation at 80° C. to 250° C., more preferably at 100° C. to 200° C.

A preferred embodiment of the present invention includes a heat-developable light-sensitive material comprising, on a support, (a) a light-sensitive silver halide, (b) a thermally decomposable organic silver salt, (c) a binder, and (d) a reducing agent.

A more preferred embodiment of the present invention includes a heat-developable color light-sensitive material comprising, on a support, (a) a light-sensitive silver halide, (b) a thermally decomposable organic silver salt, (c) a binder, and (d) a dye providing substance which is reductive and which is oxidized to imagewise release a mobile dye when heated.

Of the silver salts of carboxylic acids which undergo decarboxylation at the above described temperature, preferred examples are those represented by the following general formula (I).

$$[R-CO_2)_m] \cdot mAg \qquad (I)$$

wherein m represents an integer of 1 to 4.

R represents a substituted alkyl group having an electron attracting group at the α-position, a substituted aryl group having an electron donating group at the ortho- and/or para-position, an alkynyl group, a substituted alkynyl group, an acyl group, an alkoxycarbonyl group, an aryloxycarbonyl group, a carbamoyl group, a substituted carbamoyl group or a ring residue represented by the general formula

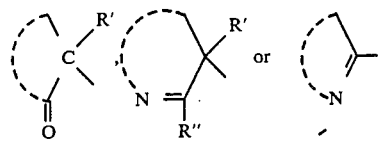

wherein a 5- or 6-member ring is present, and R' and R" are selected from the group consisting of a hydrogen atom, alkyl groups, substituted alkyl groups, aryl groups and substituted aryl groups.

Preferred examples of R are illustrated below.

The substituted alkyl group having an electron attracting group at the α-position includes:

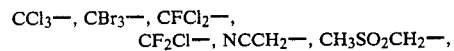

$CCl_3-$, $CBr_3-$, $CFCl_2-$, $CF_2Cl-$, $NCCH_2-$, $CH_3SO_2CH_2-$,

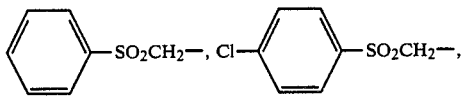

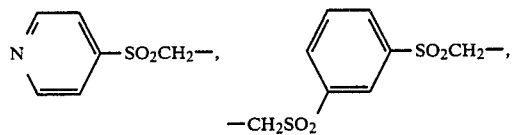

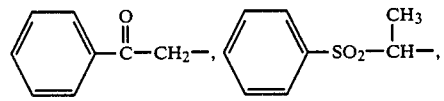

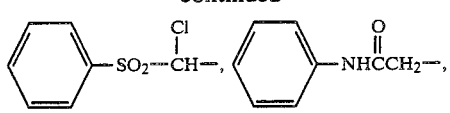
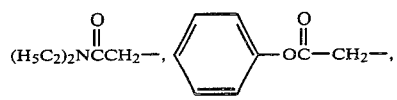
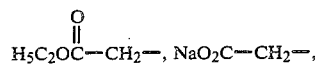
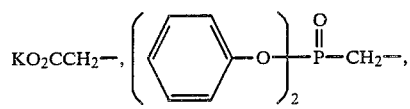
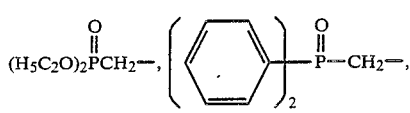
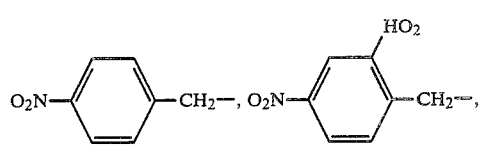
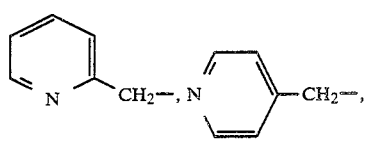
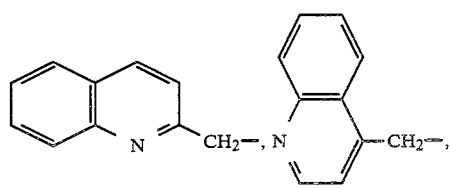
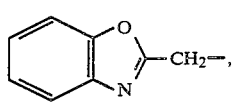
The substituted aryl group having an electron donating group at the ortho- and/or para-position includes:
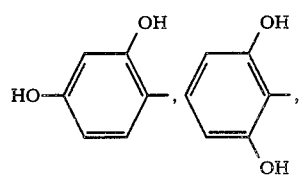
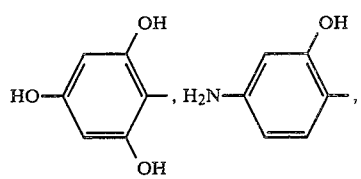
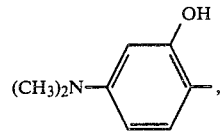
etc.
The acyl group includes:
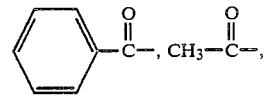
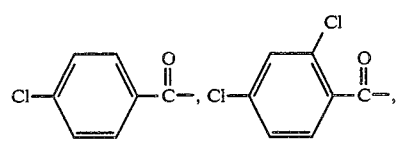
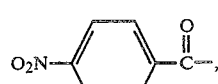
etc.
The alkoxycarbonyl group includes:
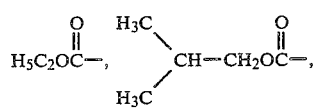
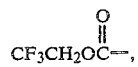
etc.
The aryloxycarbonyl group includes:
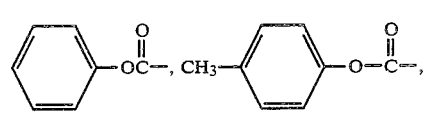
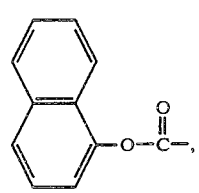
etc.
The substituted carbamoyl group includes:
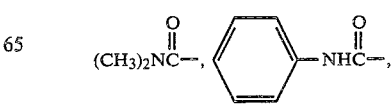

-continued

Preferred examples of

[structure]

include:

[structures]

etc.

Preferred examples of

[structure with R']

include:

[structures]

etc.

Preferred examples of

[structure with R', R"]

include:

[structures]

etc.

Preferred examples of

[structure]

include:

[structures]

etc.

In the above described general formula (I), the most preferred compounds are those wherein R represents an alkynyl group or a substituted alkynyl group, which are represented by the following general formula (II).

$$R^0 \text{+} C \equiv C - CO_2)_m \cdot mAg \qquad (II)$$

In the above described formula, $R^0$ represents a monovalent residue selected from the group consisting of a hydrogen atom, an alkyl group, a substituted alkyl group, a cycloalkyl group, an alkenyl group, an alkynyl group, an aryl group, a substituted aryl group, a heterocyclic residue, a substituted heterocyclic residue, an aralkyl group, a substituted aralkyl group, an acyl group, an alkoxycarbonyl group, a carbamoyl group, a substituted carbamoyl group, —$CO_2M$ (wherein M represents an alkali metal) and —$CO_2B$, or a divalent residue selected from the group consisting of an alkylene group, an arylene group and a heterocyclic divalent residue (which may have additionally substituents).

B is a conjugated acid of an organic base or a quaternary ammonium group. Typical examples of organic bases are guanidines, cyclic guanidines, amidines, cyclic amidines, etc.

m represents an integer of 1 to 4.

Most preferred examples of $R^0$ include a hydrogen atom, an alkyl group having 1 to 5 carbon atoms, a substituted alkyl group having 1 to 5 carbon atoms, a cycloalkyl group having 5 to 8 carbon atoms, an alkenyl group having 2 to 5 carbon atoms, an alkynyl group having 2 to 5 carbon atoms, a phenyl group, a substituted phenyl group, a naphthyl group, a substituted naphthyl group, an anthryl group, a pyridyl group, a substituted pyridyl group, a thienyl group, a substituted thienyl group, a thiazolyl group, a benzoxazolyl group, a benzothiazolyl group, an aralkyl group having 7 to 10 carbon atoms, an acyl group having 2 to 12 carbon atoms, an alkoxycarbonyl group having 2 to 9 carbon atoms, a carbamoyl group, a substituted carbamoyl group having 2 to 9 carbon atoms, —CO$_2$Na, —CO$_2$K, —CO$_2$Cs, —CO$_2$.B (B is described above), a 1,3-phenylene group, a 1,4-phenylene group, a 1,5-naphthylene group, a 2,5-thienylene group, and a 9,10-anthrylene group, etc.

R$^0$ is preferred to have a suitable electron attracting group, and an alkenyl group, an alkynyl group, a phenyl group, a substituted phenyl group, a naphthyl group, a substituted naphthyl group, an anthryl group, a pyridyl group, a substituted pyridyl group, a thienyl group, a substituted thienyl, group, a benzoxazolyl group, a benzothiazolyl group, an acyl group, an alkoxycarbonyl group, a carbamoyl group, a substituted carbamoyl group, —CO$_2$M, —CO$_2$.B (wherein B is as above defined), a phenylene group, a naphthylene group, a thienylene group and an anthrylene group, etc., are suitably used.

In the following, examples of preferred thermally decomposable organic silver salts used in the present invention are described, but the present invention is not limited thereto.

HC≡C—CO$_2$.Ag (1)

CH$_3$—C≡C—CO$_2$.Ag (2)

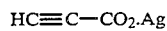 (3)

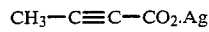 (4)

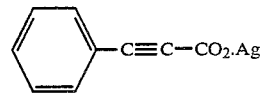 (5)

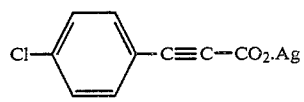 (6)

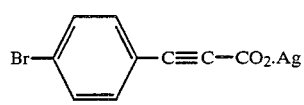 (7)

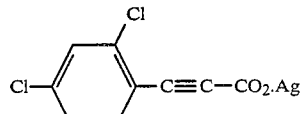 (8)

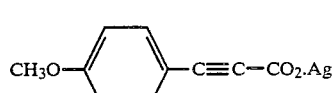 (9)

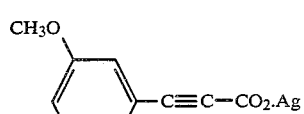

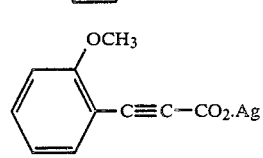

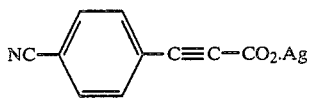 (10)

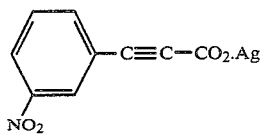 (11)

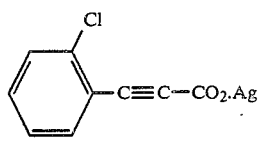 (12)

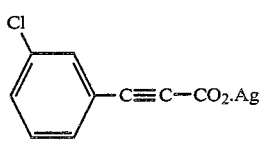 (13)

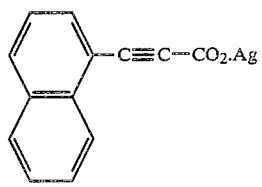 (14)

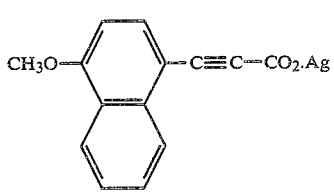 (15)

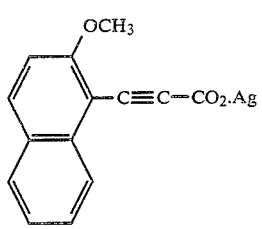 (16)

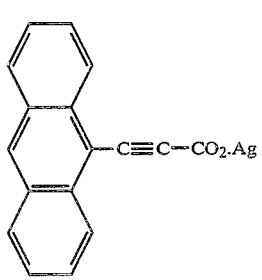 (17)

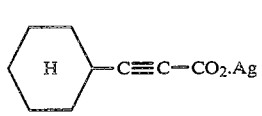 (18)

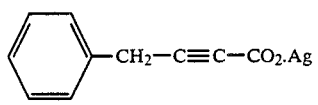 (19)
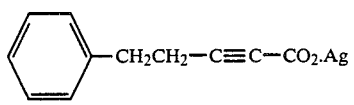 (20)
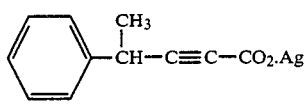 (21)
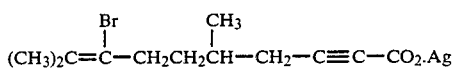 (22)
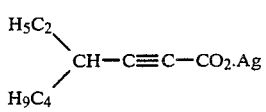 (23)
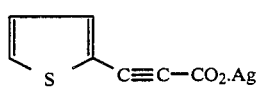 (24)
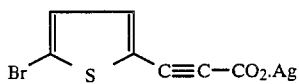 (25)
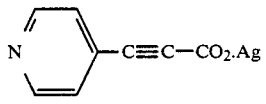 (26)
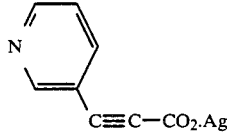 (27)
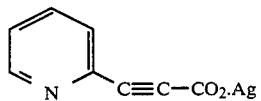 (28)
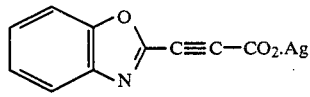 (29)
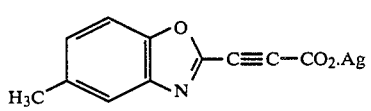 (30)
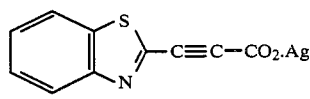 (31)
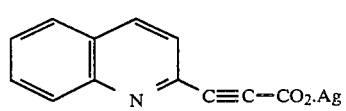 (32)
 (33)
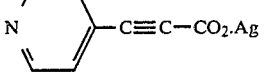 (34)
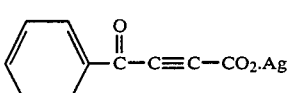 (35)
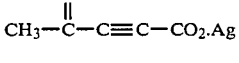 (36)
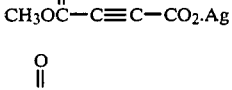 (37)
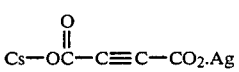 (38)
 (39)
 (40)
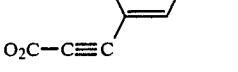 (41)
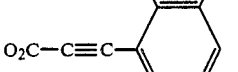 (42)
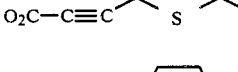 (43)
 (44)
 (45)
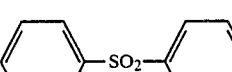

-continued

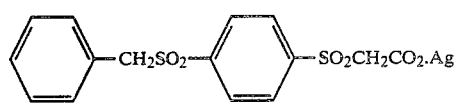 (46)

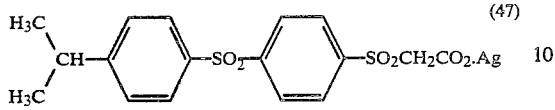 (47)

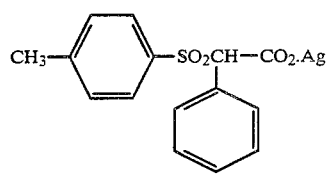 (48)

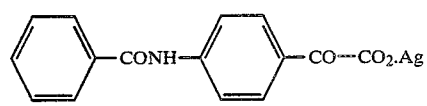 (49)

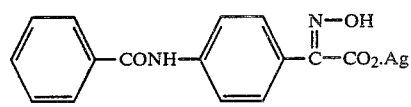 (50)

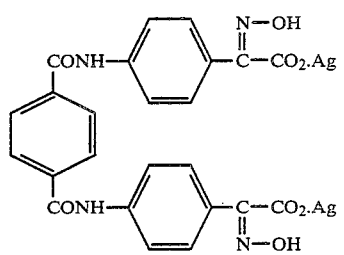 (51)

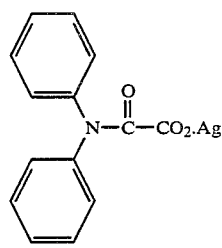 (52)

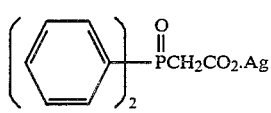 (53)

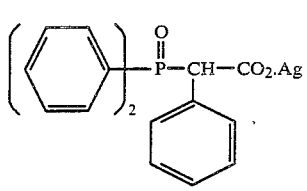 (54)

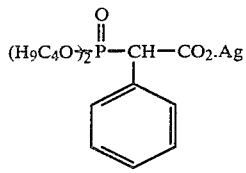 (55)

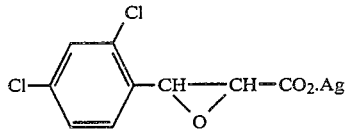 (56)

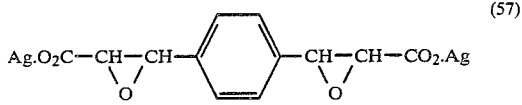 (57)

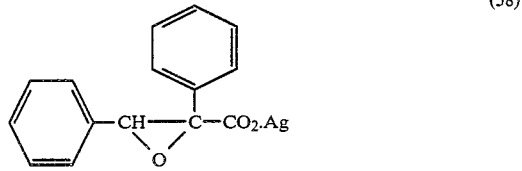 (58)

The tehrmally decomposable organic silver salts of the present invention can be prepared by synthesizing a decarboxylating carboxylic acid by the following process and mixing the acid with a silver ion donator (for example, silver nitrate).

With respect to the synthesis of decarboxylating carboxylic acids, though the process for synthesis is different according to the kind thereof, they can be synthesized in any case by known general processes. As typical examples, there is a reaction between an α-haloacetic acid and a nucleophilic agent such as a sulfinic acid salt or cyanide, etc., or a reaction between an active methyl or active methylene compound and a carbonic acid ester in the presence of a base in the case that R is a substituted alkyl group having an electron attracting group at the α-position; carboxylation by a Kolbe-Schmitt reaction in the case that R is a substituted aryl group having an electron donating group; or addition of bromine to an acrylic acid derivative and subsequent dehydrogen bromide in the case that R is an alkyl group. These reactions are described in detail in *Shinjikkenkagakukoza* 14 (II), 921–1062 (1977, Maruzen) and *Organic Fucntional Group Preparations*, 196–268 (1968, Academic Press).

In the case of comparatively simple substances such as trihaloacetic acid, phenylacetic acid derivatives or α-ketocarboxylic acids, etc., those commercially available can be used directly.

Examples of synthesizing thermally decomposable organic silver salts are hereinafter described.

SYNTHESIS OF ORGANIC SILVER SALT (3)

29.6 g of cinnamic acid was dissolved in 80 ml of acetic acid with heating, and 32 g of bromine was then added dropwise thereto. After stirring at 50° C. for 15 minutes, it was allowed to cool and 100 ml of water was gradually added thereto. The formed white crystals were filtered off, washed with water and dried. Yield: 56 g.

56 g of potassium hydroxide was dissolved in 200 ml of methanol, and the above described crystals were slowly added thereto. Methanol was removed by heating on a water bath with stirring. The residue was dissolved in 200 ml of water and neutralized with diluted sulfuric acid while ice cooling. The separated light yellow oil solidified rapidly. The solidified crystals were filtered off and recrystallized from water to obtain 22 g of phenylpropiolic acid. Melting Point: 135°–137° C.

The above described acid was converted into the desired silver salt by a conventional process.

SYNTHESIS OF ORGANIC SILVER SALT (45)

33 g of potassium hydroxide was added to a mixture of 26.2 g of thioglycolic acid and 150 ml of toluene, and the mixture was stirred with heating.

The formed water was distilled away together with toluene. When water was not present, 100 ml of dimethylacetamide was added thereto and 59.4 g of p-bromodiphenylsulfone was then slowly added. After stirring at 150°–160° C. for 3 hours, the reaction solution was allowed to cool and poured into cold diluted hydrochloric acid. The separated oil was extracted with ethyl acetate, and the extract solution was washed with water. After being dried, it was concentrated under reduced pressure to remove ethyl acetate, and the separated crystals were filtered off and washed with toluene. Yield: 44 g.

A mixture of 40 g of the above described crystals, 0.2 g of sodium tungstate.dihydrate and 120 ml of acetic acid was heated to 50° C., and 30 ml of a 35% aqueous solution of hydrogen peroxide was added dropwise thereto at 50°–60° C. After dropwise addition, the mixture was stirred at 75° C. for 30 minutes, and thereafter it was allowed to cool and the reaction solution was poured into cold water. The separated white crystals were filtered off, washed with water and dried to obtain 41 g of (p-phenylsulfonylphenyl)sulfonylacetic acid. Melting Point: 194°–196° C. (decomposition).

The above described acid was converted into silver salt by a conventional process.

SYNTHESIS OF ORGANIC SILVER SALT (53)

To 400 ml of dried ether, 21.6 g of finely divided diphenylmethylphosphine oxide was added, and a solution of butyl lithium hexane in an amount corresponding to 0.1 mol thereof was slowly added with vigorous stirring. After the reaction mixture was refluxed for 3 hours with heating, it was cooled to 20° C., and slowly added to a mixture of 100 g of finely crushed dry ice and 300 ml of ether.

After stirring for 10 minutes, the ether was distilled away. Diluted hydrochloric acid was added to the residue and it was extracted with ethyl acetate. The ethyl acetate extract solution was repeatedly extracted with a 5% aqueous solution of sodium hydrogen-carbonate, and the extract solution was acidified with diluted hydrochloric acid. The separated white crystals were filtered off, washed with water and dried to obtain 16.8 g of carboxymethyl diphenylphosphine oxide. Melting Point: 143°–146° C. This free acid was then converted into silver salt by a conventional process to obtain Organic Silver Salt (53).

The thermally decomposable organic silver salt may be prepared in the same system, namely, together with other components for the heat-developable light-sensitive material in combination, or may be prepared out of the system, namely, separately from the other components for the heat-developable light-sensitive material. However, considering easy control in the case of preparation or ease of storage, it is preferable to prepare it separately from the other components for the heat-developable light-sensitive material.

Salts composed of decarboxylating carboxylic acid and silver can also be obtained by mixing a silver ion source such as silver nitrate with a decarboxylating carboxylic acid in a hydrophilic solvent such as water and/or methanol. In this case, mixing may be carried out in the presence of a hydrophilic binder such as gelatin. Purification of the resultant product or dispersion can be carried out according to procedures known in this field.

Two or more kinds of organic silver salts of the present invention can be used. Further, they can be used together with known organic silver salts. The organic silver salts of the present invention may be used in a layer containing light-sensitive silver halide or may be used in an adjacent layer thereof.

The organic silver salts of the present invention can be used in a concentration over a wide range. A suitable amount to be coated is 10 mg to 10 g/m$^2$ as silver. It is in the range of 0.01 to 200 mols based on light-sensitive silver halide. The sahpe and particle size of the organic silver salts of the present invention are selected arbitrarily, but it is preferred that the average particle size be 10 μm or less.

In the present invention, various image forming substances can be used.

Heat-developable light-sensitive materials and processes thereof have been described in the prior art now discussed, and they find application with the present invention, for example, *Shashinkogaku no Kiso* (published by Corona Co., 1979), pages 553–555, *Gazojoho*, page 40, published in April 1978, *Nebletts Handbook of Photography and Reprography*, 7th Ed. (Van Nostrand Reinhold Company), pages 32–33, U.S. Pat. Nos. 3,152,904, 3,301,678, 3,392,020 and 3,457,075, British Pat. Nos. 1,131,108 and 1,167,777 and *Research Disclosure* (June 1978), pages 9–15 (RD-17029).

With respect to processes for obtaining dye images (color images), there are forming dye images by combining an oxidation product of a developing agent with couplers, e.g., using p-phenylenediamine reducing agents and phenolic or active methylene couplers per U.S. Pat. No. 3,531,286, p-aminophenol type reducing agents per U.S. Pat. No. 3,761,270, sulfonamidophenol type reducing agents per Belgian Pat. No. 802,519 and *Research Disclosure* (September 1975), pages 31 and 32, and combinations of sulfonamidophenol type reducing agent and 4-equivalent type couplers per U.S. Pat. No. 4,021,240.

As couplers used in the above described image formation process, there are those described in the above described cited patents. Further, color couplers used in liquid development processing known hitherto can be used. These couplers are compounds capable of coloring by oxidative coupling with, for example, aromatic primary amine developing agents (for example, phenylenediamine derivatives or aminophenol derivatives, etc.), and typical examples are as follows. For example, as magenta couplers, there are 5-pyrazolone couplers, pyrazolobenzimidazole couplers, cyanoacetylcoumarone couplers and opened chain acylacetonitrile couplers. As yellow couplers, there are acylacetamide couplers (for example, benzoylacetanilides, and pivaloylacetanilides), etc. As cyan couplers, there are naphthol couplers and phenol couplers, etc. It is preferred that these couplers be nondiffusible substances which have a hydrophobic group called a ballast group in the molecule or be polymerized substances. The couplers may be any of the 4-equivalent type and 2-equivalent type to silver ions. Further, they may be colored couplers having a color correction effect or couplers which release a development restrainer by development (DIR couplers).

A process for forming images in which mobile dyes are released by utilizing a coupling reaction of a reducing agent oxidized by an oxidation reduction reaction with a silver halide or an organic silver salt at a high temperature has been described in European Pat. No. 79,056, West German Pat. No. 3,217,853 and European Pat. No. 67,455.

Further, a process in which a nitrogen-containing heterocyclic group is introduced into dyes and a silver salt is formed to release dyes by heat development has been described in *Research Disclosure* (May 1978), pages 54–58 (RD-16966).

In addition, a process for forming positive color images by an exposed silver dye bleaching process has been described in, for example, *Research Disclosure* (April 1976), pages 30–32 (RD-14433) and (December 1976), pages 14–15 (RD-15227) and U.S. Pat. No. 4,235,957, etc., wherein useful dyes and manners of bleaching are described.

Further, a process for forming color images utilizing leuco dyes has been described in, for example, U.S. Pat. Nos. 3,985,565 and 4,022,617.

Moreover, in recent years, various new materials and processes for forming color images by heat development have been proposed, and these materials are particularly suitably used in the present invention. A process using dye providing substances which release a mobile dye as a result of an oxidation reduction reaction with a silver halide or an organic silver salt at high temperature has been described in European Pat. No. 76,492, West German Pat. No. 3,215,485, European Pat. No. 66,282, Japanese Patent Application (OPI) Nos. 65839/84 and 152440/84 (the term "OPI" as used herein refers to a "published unexamined Japanese patent application").

As dye providing substances used in the above described processes, there are the following.

Dye providing substances useful in the present invention are represented by the following formula (III).

$$D-Y \quad (III)$$

wherein D represents a dye part or a precursor thereof, and Y represents a substrate having a function of changing the diffusibility of the dye providing substance (III) by an oxidation reduction reaction caused in the heat development process. The term "changing diffusibility" means (1) compound (III) which is essentially nondiffusible changes into a diffusible compound or releases a diffusible dye, or (2) compound (III) which is essentially diffusible changes into a nondiffusible compound. Further, depending upon the properties of Y, this change is caused by oxidation of Y or is caused by a reduction thereof. Both can be suitably used.

As examples of changing diffusibility by oxidation of Y, one can use dye releasing redox substrates such as p-sulfonamidonaphthols (including p-sulfonamidophenols, described in Japanese Patent Application (OPI) Nos. 33826/73 and 50736/78 and European Pat. No. 76,492), o-sulfonamidophenols (including o-sulfonamidophenols, described in Japanese Patent Application (OPI) Nos. 113624/76, 12642/81, 16130/81, 16131/81, 4043/82 and 650/82, U.S. Pat. No. 4,053,312 and European Pat. No. 76,492), hydroxysulfonamide hetero rings (Japanese Patent Application (OPI) No. 104343/76 and European Pat. No. 76,492) or 3-sulfonamidoindoles (described in Japanese Patent Application (OPI) Nos. 104343/76, 46730/78, 130122/79 and 85055/82 and European Pat. No. 76,492), etc.

As other examples, releasing dyes by intramolecular nucleophilic attack after oxidation of Y can be used, e.g., intramolecular assist type substrates described in Japanese Patent Application (OPI) No. 20735/82 and Japanese Patent Application No. 177148/82 (corresponding to U.S. Ser. No. 540,737 filed on Oct. 11, 1983).

Further, as other examples, there are substrates which release a dye by an intramolecular ring-closure reaction under a basic conditions but do not substantially cause release of the dye when Y is oxidized (described in Japanese Patent Application (OPI) No. 63618/76). As a modification, substrates which release a dye by recyclization of isoxazolone ring by a nucleophilic agent (described in Japanese Patent Application (OPI) Nos. 111628/74 and 4819/77).

Further, as other examples, there are substrates which release a dye moiety by dissociation of an acid proton under basic conditions but do not substantially release the dye when Y is oxidized (described in Japanese Patent Application (OPI) Nos. 69033/78 and 130927/79).

On the other hand, as examples of changing diffusibility by reduction of Y, there are nitro compounds described in Japanese Patent Application (OPI) No. 110827/78 and quinone compounds described in Japanese Patent Application (OPI) No. 110827/78 and U.S. Pat. Nos. 4,356,249 and 4,358,525. They are compounds which are reduced by a reducing agent (called an electron donor) remaining in the heat development process without being consumed and release a dye by molecular attack of the nucleophilic group formed as a result of the reduction. As a modification, quinone type substrates wherein the dye moiety is released by dissociation of an acid proton of the reduced material are useful (described in Japanese Patent Application (OPI) Nos. 130927/79 and 164342/81). In the case of using the above described substrates wherein diffusibility changes by reduction, it is essential to use a suitable reducing agent (an electron donor) which intermediates between a silver salt oxidizing agent and a dye providing substance, and examples thereof are described in the above mentioned references. Further, substrates in which an electron donor is present in the substrate Y (called an LDA compound) are also useful.

Further, as other image forming materials, materials wherein the mobility of the compound having a dye moiety changes as a result of an oxidation reduction reaction with silver halide or organic silver salt at a high temperature can be used, which have been described in Japanese Patent Application No. 39400/83.

In addition, materials which release a mobile dye by a reaction with silver ion in the light-sensitive material have been described in Japanese Patent Application No. 55692/83.

Many of the above described materials are materials wherein an imagewise distribution of mobile dyes corresponding to exposure is formed in the light-sensitive material by heat development, and processes of obtaining visible images by transferring the dyes of image to a dye fixing material (the so-called diffusion transfer) have been described in the above described cited patents and Japanese Patent Application Nos. 42092/83 and 55172/83 (corresponding to U.S. Ser. No. 590,592 filed on Mar. 16, 1984), etc.

The dye providing substance used in the present invention can be introduced into a layer of the light-sensitive material by known methods such as a method as described in U.S. Pat. No. 2,322,027. In this case, an organic solvent having a high boiling point or an organic solvent having a low boiling point as described below can be used. For example, the dye providing substance is dispersed in a hydrophilic colloid after being dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a boiling point of about 30° C. to 160°0 C., for example, a lower alkyl acetate such as ethyl acetate, butyl acetate, etc., ethyl propionate, secondary butyl alcohol, methyl isobutyl ketone, β-ethoxyethyl acetate, methyl cellosolve acetate, cyclohexanone, etc. The above described organic solvents having a high boiling point and organic solvents having a low boiling point may be used as a mixture thereof.

Further, it is possible to use a dispersion method using a polymer as described in Japanese Patent Publication No. 39853/76 and Japanese Patent Application (OPI) No. 59943/76. Moreover, various surface active agents can be used when the dye providing substance is dispersed in a hydrophilic colloid. For this purpose, the surface active agents illustrated in other parts of the specification can be used.

An amount of the organic solvent having a high boiling point used in the present invention is 10 g per g of the dye providing substance used or less, preferably 5 g per g or less.

Among the dye providing substances represented by the general formula (III), a dye providing substance which releases a mobile dye used in the present invention can be represented by the following general formula (IV):

$$R_a\text{—}SO_2\text{—}D \qquad \text{(IV)}$$

wherein $R_a$ represents a reducing group, and D represents an image forming dye moiety containing a hydrophilic group.

The above described substances are oxidized in correspondence or countercorrespondence to the latent image which is imagewise distributed in the silver halide to imagewise release a mobile dye.

Preferably the reducing group ($R_a$) in the dye providing substance $R_a$—$SO_2$—D has an oxidation reduction potential to a saturated calomel electrode of 1.2 V or less when measuring the polarographic half wave potential using acetonitrile as a solvent and sodium perchlorate as a base electrolyte. Preferred examples of the reducing group ($R_a$) include those represented by the following general formulae (V) to (XII).

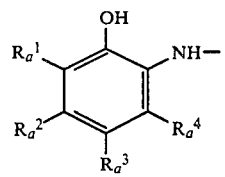
(V)

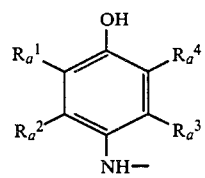
(VI)

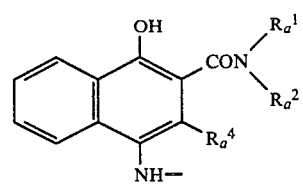
(VII)

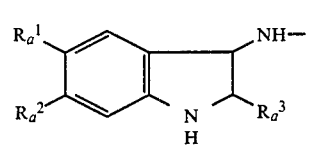
(VIII)

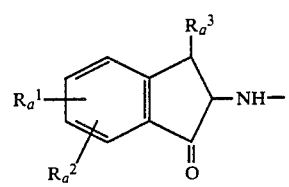
(IX)

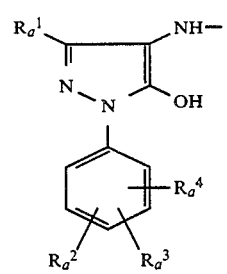
(X)

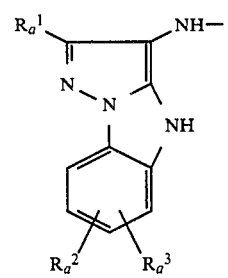
(XI)

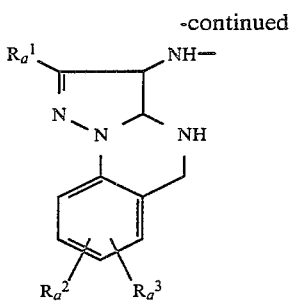

wherein $R_a^1$, $R_a^2$, $R_a^3$ and $R_a^4$ each represents a hydrogen atom or a substituent selected from an alkyl group, a cycloalkyl group, an aryl group, an alkoxy group, an aryloxy group, an aralkyl group, an acyl group, an acylamino group, an alkylsulfonylamino group, an arylsulfonylamino group, an aryloxyalkyl group, an alkoxyalkyl group, an N-substituted carbamoyl group, an N-substituted sulfamoyl group, a halogen atom, an alkylthio group or an arylthio group.

The alkyl moiety and the aryl moiety in the above described substituents may be further substituted with an alkoxy group, a halogen atom, a hydroxy group, a cyano group, an acyl group, an acylamino group, a substituted carbamoyl group, a substituted sulfamoyl group, an alkylsulfonylamino group, an arylsulfonylamino group, a substituted ureido group or a carboalkoxy group.

Furthermore, the hydroxy group and the amino group included in the reducing group represented by $R_a$ may be protected by a protective group capable of reproducing the hydroxy group and the amino group by the action of a nucleophilic agent.

In more preferred embodiments of the present invention, the reducing group $R_a$ is represented by the following general formula (XIII).

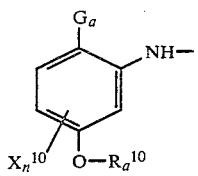

wherein $G_a$ represents a hydroxy group or a group giving a hydroxy group upon hydrolysis; $R_a^{10}$ represents an alkyl group or an aromatic group; n represents an integer of 1 to 3; $X^{10}$ represents an electron donating substituent when n is 1 or substituents, which may be the same or different, one of the substituents being an electron donating group and the second or second and third substituents being selected from an electron donating group or a halogen atom when n is 2 or 3, respectively; $X^{10}$ groups may form a condensed ring with each other or with $OR_a^{10}$; and the total number of the carbon atoms included in $R_a^{10}$ and $X^{10}$ is not less than 8.

Specific examples of the reducing groups in the above described general formula (XIII) are described in U.S. Pat. No. 4,055,428, Japanese Patent Application (OPI) Nos. 12642/81 and 16130/81, respectively.

In other more preferred embodiments of the present invention, the reducing group ($R_a$) is represented by the following general formula (XIV).

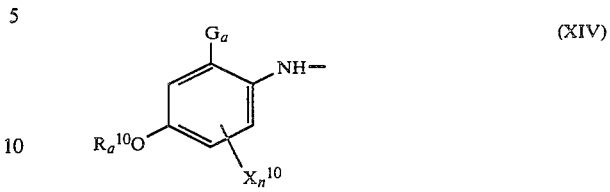

wherein $G_a$, $X^{10}$, $R_a^{10}$ and n each has the same meaning as $G_a$, $X^{10}$, $R_a^{10}$ and n defined in the general formula (XIII).

In still other more preferred embodiments of the present invention, the reducing group ($R_a$) is represented by the following general formula (XV).

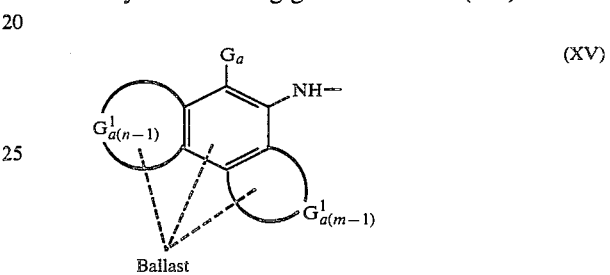

wherein Ballast represents a group which renders the compound nondiffusible.

$G_a$ represents a hydroxyl group or a precursor of a hydroxyl group.

$G_a^1$ represents an aromatic ring and represents a group which forms a naphthalene ring together with a benzene ring. n and m each represents a different integer of 1 or 2.

Examples included in the above described (XV) are described in U.S. Pat. No. 4,053,312.

Reductive substrates of the formulae (VIII), (X), (XI) and (XII) are characterized by containing a heterocyclic ring. As examples, there are those described in U.S. Pat. No. 4,198,235, Japanese Patent Application (OPI) No. 46730/78, U.S. Pat. No. 4,273,855. Examples of the reductive substrates represented by the formula (IX) are described in U.S. Pat. No. 4,149,892.

As dyes capable of being utilized as image forming dyes (D), there are azo dyes, azomethine dyes, anthraquinone dyes, naphthoquinone dyes, styryl dyes, nitro dyes, quinoline dyes, carbonyl dyes and phthalocyanine dyes, etc. These dyes can also be used in the form of having temporarily shorter wavelengths, the color of which is recoverable in the development processing.

Dye providing substances used in the present invention can be synthesized according to the synthetic process described in European Patent Publication (unexamined) No. 76,492.

Examples of dye image forming substances used in the present invention have been described in the aforementioned patents. Since all suitable compounds cannot be enumerated herein, only some of them are shown as examples. For example, as dye providing substances represented by the above described formula (IV), there are the following.

(1)
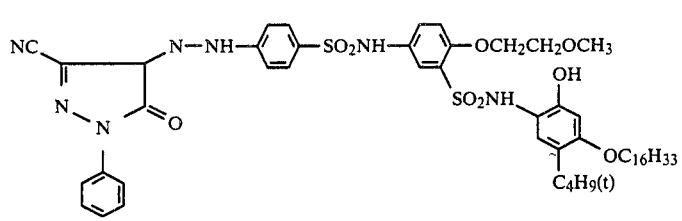
(2)
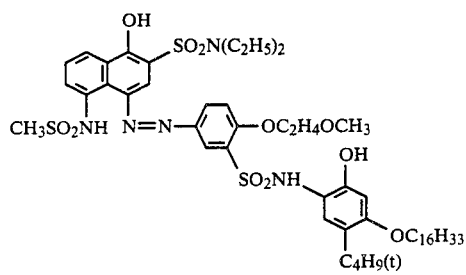
(3)
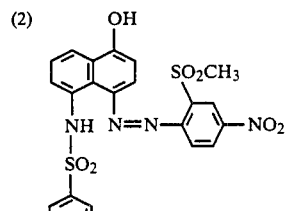
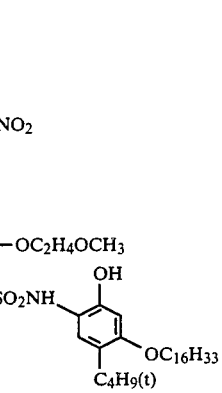
(4)
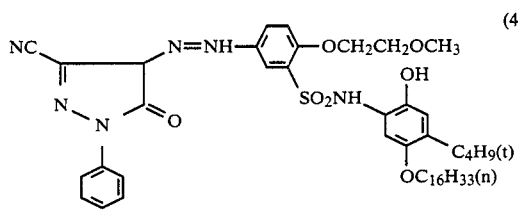
(5)
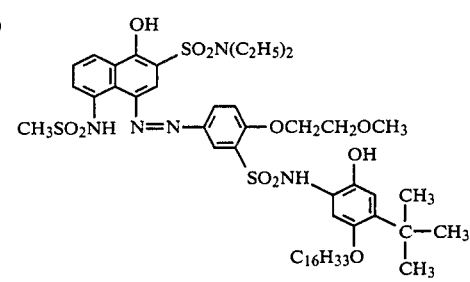
(6)
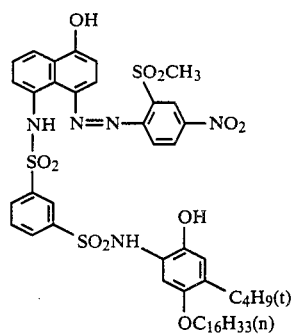
(7)
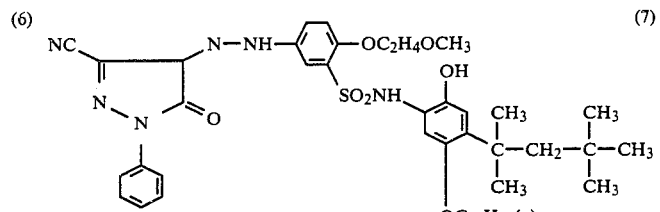
(8)
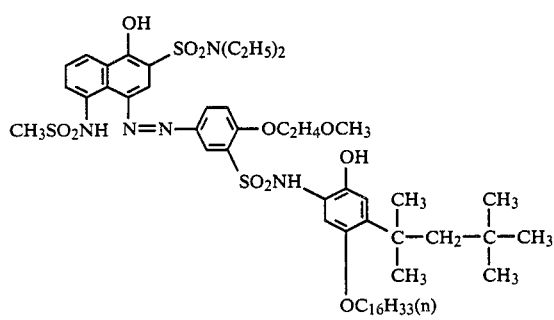
(9)
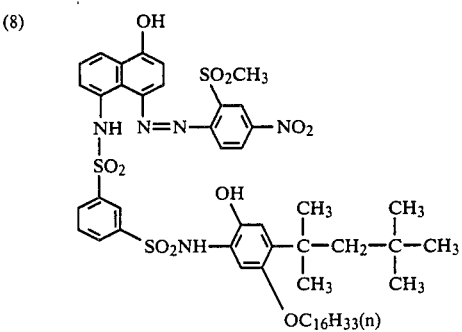

-continued

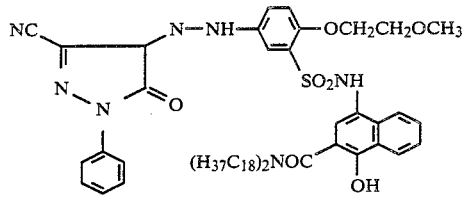 (10)

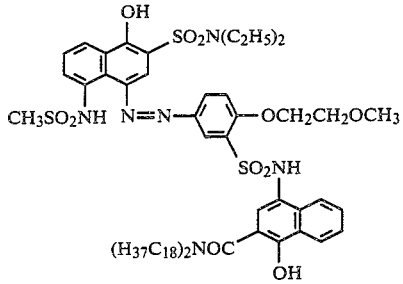 (11)

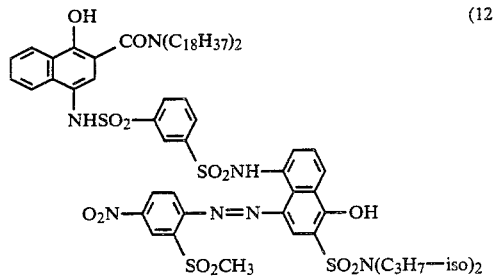 (12)

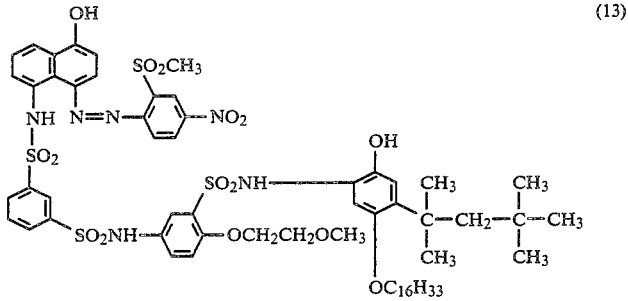 (13)

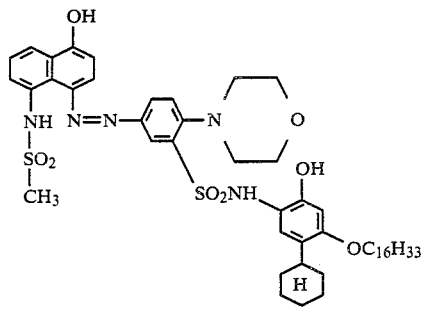 (14)

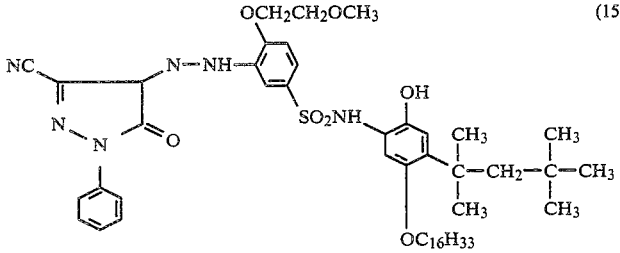 (15)

The above described compounds are merely examples, and the compounds used in the present invention are not to be construed as limited thereto.

The silver halide used in the present invention includes silver chloride, silver chlorobromide, silver chloroiodide, silver bromide, silver iodobromide, silver chloroiodobromide and silver iodide, etc.

The process for preparing those silver halides is explained taking the case of silver iodobromide. That is, the silver iodobromide is prepared by first adding a silver nitrate solution to a potassium bromide solution to form silver bromide particles and then adding potassium iodide to the mixture.

Two or more kinds of silver halides in which the particle size and/or the silver halide composition are different from each other may be used in mixture.

The average particle size of the silver halide used in the present invention is preferably from 0.001 $\mu$m to 10 $\mu$m, more preferably from 0.001 $\mu$m to 5 $\mu$m.

The silver halide used in the present invention may be used as is. However, it may be chemically sensitized with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

A suitable coating amount of the light-sensitive silver halide employed in the present invention is from 1 mg/m$^2$ to 10 g/m$^2$ calculated as silver.

The reducing agents used in the present invention include the following compounds.

Hydroquinone compounds (for example, hydroquinone, 2,5-dichlorohydroquinone, 2-chlorohydroquinone, etc.), aminophenol compounds (for example, 4-aminophenol, N-methylaminophenol, 3-methyl-4-aminophenol, 3,5-dibromoaminophenol, etc.), catechol compounds (for example, catechol, 4-cyclohexylcatechol, 3-methoxycatechol, 4-(N-octadecylamino)catechol, etc.), phenylenediamine compounds (for example, N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine, etc.).

Examples of more preferred reducing agents include the following compounds.

3-Pyrazolidone compounds (for example, 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone).

Various combinations of developing agents as described in U.S. Pat. No. 3,039,869 can also be used.

In the present invention, an amount of reducing agent added is from 0.01 mol to 20 mols per mol of silver and more preferably from 0.1 mol to 10 mols per mol of silver.

In the present invention, if necessary, an auxiliary developing agent can be used although providing substance is present. The auxiliary developing agent in this case is a compound which is oxidized by the silver halide to form its oxidized product having the ability to oxidize the reducing group in the dye providing substance.

Examples of useful auxiliary developing agents include hydroquinone, alkyl substituted hydroquinones such as t-butylhydroquinone, 2,5-dimethylhydroquinone, etc., catechols, pyrogallols, halogen substituted hydroquinones such as chlorohydroquinone, dichlorohydroquinone, etc., alkoxy substituted hydroquinones such as methoxyhydroquinone, and polyhydroxybenzene derivatives such as methyl hydroxynaphthalene, etc. Further, methyl gallate, ascorbic acid, ascorbic acid derivatives, hydroxylamines such as N,N'-di(2-ethoxyethyl)hydroxylamine, etc., pyrazolidones such as 1-phenyl-3-pyrazolidone, 4-methyl-4-hydroxymethyl-1-phenyl-3-pyrazolidone, etc., reductones and hydroxy tetronic acids are useful.

The auxiliary developing agent is used in an appropriate amount. A suitable concentration range is generally 0.0005 times by mol to 20 times by mol based on the amount of silver. A particularly suitable range is 0.001 times by mol to 4 times by mol.

The binder which can be used in the present invention can be employed individually or in a combination thereof. A hydrophilic binder can be used as the binder according to the present invention. The typical hydrophilic binder is a transparent or translucent hydrophilic colloid, examples of which include natural substances, for example, a protein such as gelatin, a gelatin derivative, a cellulose derivative, etc., a polysaccharide such as starch, gum arabic, etc., and a synthetic polymer, for example, a water-soluble polyvinyl compound such as polyvinyl pyrrolidone, acrylamide polymer, etc. Another example of the synthetic polymer compound is a dispersed vinyl compound in a latex form which is used for the purpose of increasing dimensional stability of a photographic material.

The silver halide used in the present invention can be spectrally sensitized with methine dyes or other dyes. Usually, the silver halide is spectrally sensitized to green light or red light but it sometimes is desirable that the silver halide has sensitivity to infrared range. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, are useful in these dyes, e.g., a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may also be substituted.

To merocyanine dyes and complex merocyanine dyes, as nuclei having a ketomethylene structure, 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be used.

Useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, etc.

These sensitizing dyes can be employed individually, and can also be employed in combination thereof. A combination of sensitizing dyes is often used, particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

Furhter, in the present invention, it is possible to use a compound which activates development simultaneously while stabilizing the image. Particularly, it is preferred to use isothiuroniums including 2-hydroxyethylisothiuronium.trichloroacetate as described in U.S. Pat. No. 3,301,678, bisisothiuroniums including 1,8-(3,6-dioxaoctane)-bis(isothiuronium.trifluoroacetate), etc., as described in U.S. Pat. No. 3,669,670, thiol compounds as described in West German Patent Application (OLS) No. 2,162,714, thiazolium compounds such as 2-amino-2-thiazolium.trichloroacetate, 2-amino-5-bromoethyl-2-thiazolium.trichloroacetate, etc., as described in U.S. Pat. No. 4,012,260, compounds having α-sulfonylacetate as an acid moiety such as bis(2-amino-2-thiazolium)methylene-bis(sulfonylacetate), 2-amino-2-thiazolium phenylsulfonylacetate, etc., as described in U.S. Pat. No. 4,060,420, and compounds having 2-carboxycarboxamide as an acid moiety as described in U.S. Pat. No. 4,088,496.

In addition, azole thioether and blocked azoline thione compounds described in Belgian Pat. No. 768,071, 4-aryl-1-carbamoyl-2-tetrazoline-5-thione compounds described in U.S. Pat. No. 3,893,859 and compounds described in U.S. Pat. Nos. 3,839,041, 3,844,788 and 3,877,940 are suitably used.

In the present invention, image toning agents can be incorporated, if desired. Effective toning agents are compounds such as 1,2,4-triazole, 1H-tetrazole, thiouracil and 1,3,4-thiadiazole, etc. Examples of preferred toning agents include 5-amino-1,3,4-thiadiazole-2-thiol, 3-mercapto-1,2,4-triazole, bis(dimethylcarbamoyl)disulfide, 6-methylthiouracil and 1-phenyl-2-tetrazoline-5-thione, etc. Particularly effective toning agents are compounds which form black images.

The concentration of the toning agents incorporated varies according to the kind of heat-developable light-sensitive material, processing conditions, images to be required, and other factors, but it is generally in a range of about 0.001 to 0.1 mol per mol of silver in the light-sensitive material.

In the present invention, various dye releasing assistants can be used. As the dye releasing assistants, bases or base precursors which are compounds, showing a basic property, capable of accelerating development or compounds having the so-called nucleophilic property.

The dye releasing assistants can be used in any of the light-sensitive materials and dye fixing materials. In the case of incorporating them in light-sensitive materials, it is particularly advantageous to use base precursors. The term: base precursor means a substance which releases a base component by heating, wherein the base component released may be any inorganic base or organic base.

As examples of preferred bases, there are, as inorganic bases, hydroxides, secondary or tertiary phosphates, boric acid salts, carbonates, quinolinic acid salts, and metaboric acid salts of alkali metals or alkaline earth metals; ammonium hydroxide; quaternary alkylammonium hydroxide; and other metal hydroxides; and, as organic salts, aliphatic amines (trialkylamines, hydroxylamines and aliphatic polyamines), aromatic amines (N-alkyl substituted aromatic amines, N-hydroxyalkyl substituted aromatic amines and bis[p-(dialkylamino)phenyl]methanes), heterocyclic amines, amidines, cyclic amidines, guanidines and cyclic guanidines, etc. Further, betaine tetramethylammonium iodide and diaminobutane dihydrochloride described in U.S. Pat. No. 2,410,644 and organic compounds including urea and amino acids such as 6-aminocaproic acid described in U.S. Pat. No. 3,506,444 are useful. In the present invention, compounds having a Ka value of 8 or more are particularly useful.

As the base precursors, substances which undergo reaction by heating to release a base, such as salts of an organic acid which is decarboxylated by heating to cause decomposition and a base, or compounds which are decomposed by Lossen rearrangement or Beckman rearrangement to release an amine, are used.

As preferred base precursors, there are precursors of the above described bases. For example, there are salts of thermally decomposable organic acid such as trichloroacetic acid, trifluoroacetic acid, propiolic acid, cyanoacetic acid, sulfonylacetic acid or acetoacetic acid, etc., and salts of 2-carboxycarboxamide described in U.S. Pat. No. 4,088,496, etc.

Preferred examples of the base precursors are described. As examples of compounds which are believed to release a base by decarboxylation of the acid moiety, there are the following.

As trichloroacetic acid derivatives, there are guanidine trichloroacetic acid, piperidine trichloroacetic acid, morpholine trichloroacetic acid, p-toluidine trichloroacetic acid and 2-picoline trichloroacetic acid, etc.

In addition, base precursors described in British Pat. No. 998,945, U.S. Pat. No. 3,220,846 and Japanese Patent Application (OPI) No. 22625/75, etc., can be used.

As substances besides trichloroacetic acids, there are 2-carboxycarboxamide derivatives described in U.S. Pat. No. 4,088,496, α-sulfonylacetate derivatives described in U.S. Pat. No. 4,060,420 and salts of propiolic acid derivatives and bases described in Japanese Patent Application No. 55700/83 (corresponding to U.S. Ser. No. 595,121 filed on Mar. 30, 1984), etc. Salts using alkali metal and alkaline earth metal as a base component besides organic bases are also available and described in Japanese Patent Application No. 69597/83 (corresponding to U.S. Ser. No. 601,758 filed on Apr. 19, 1984).

As other precursors, hydroxamic carbamates described in Japanese Patent Application No. 43860/83 (corresponding to U.S. Ser. No. 590,396 filed on Mar. 16, 1984) utilizing Lossen rearrangement and aldoxime carbamates described in Japanese Patent Application No. 31614/83 (corresponding to U.S. Ser. No. 583,913 filed on Feb. 27, 1984) which form nitrile, etc., are available.

Further, amineimides described in Research Disclosure, No. 15776 (May 1977) and aldonic amides described in Japanese Patent Application (OPI) No. 22625/75 are suitably used, because they form a base by decomposition at a high temperature.

These bases and base precursors can be used over a wide range. An effective range is less than 50% by weight of the weight of the dried coating film in the light-sensitive material, and, preferably, a range from 0.01% by weight to 40% by weight.

It is of course possible to use the above described bases or base precursors not only for dye release acceleration but also for other purposes, for example, control of pH value.

In the present invention, it is possible to use a thermal solvent. The term "thermal solvent" means a non-hydrolyzable organic material which is solid at an ambient temperature but melts together with other components at a temperature of heat treatment or below. Preferred examples of thermal solvents include compounds which can act as a solvent for the developing agent and compounds having a high dielectric constant which accelerate physical development of silver salts. Examples of preferred thermal solvents include polyglycols as described in U.S. Pat. No. 3,347,675, for example, polyethylene glycol having an average molecular weight of 1,500 to 20,000, derivatives of polyethylene oxide such as polyethylene oxide oleic acid ester, etc., beeswax, monostearin, compounds having a high dielectric constant which have an $-SO_2-$ or $-CO-$ group such as acetamide, succinimide, ethylcarbamate, urea, methylsulfonamide or ethylene carbonate, polar substances as described in U.S. Pat. No. 3,667,959, lactone of 4-hydroxybutanoic acid, methylsulfinylmethane, tetrahydrothiophene-1,1-dioxide, and 1,10-decanediol, methyl anisate and biphenyl suberate as described in Research Disclosure, pages 26 to 28 (December, 1976), etc.

Examples of various additives which also can be used include those described in *Research Disclosure*, Vol. 170, No. 17029 (June, 1978), for example, plasticizers, dyes for improving sharpness, antihalation dyes, sensitizing dyes, matting agents, fluorescent whitening agents and fading preventing agent, etc.

A protective layer, an intermediate layer, a subbing layer, a back layer and other layers can be produced by preparing each coating solution and applying to a support by various coating methods such as a dip coating method, an air-knife coating method, a curtain coating method or a hopper coating method as described in U.S. Pat. No. 2,681,294 and drying in the same manner as used in preparing the heat-developable light-sensitive layer of the present invention, by which the light-sensitive material is obtained.

If necessary, two or more layers may be applied at the same time by the method as described in U.S. Pat. No. 2,761,791 and British Pat. No. 837,095.

In the photographic light-sensitive material and the dye fixing material of the present invention, the photographic emulsion layer and other binder layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloylhexahydro-s-triazine, 1,3-vinylsulfonyl-2-propanol, etc.), active halogen compounds (2,4-dichloro-6-hydroxy-s-triazine, etc.), mucohalogenic acids (mucochloric acid, mucophenoxychloric acid, etc.), etc., which are used individually or as a combination thereof.

The above described components composing the heat-developable light-sensitive materials of the present invention can be arranged in arbitrarily suitable positions. For example, one or more components can be arranged in one or more film layers in the light-sensitive material, if necessary. In some cases, it is desirable to incorporate the above described reducing agents, image stabilizers and/or other additives in the protective layer in specified amounts (rates). Such a case is sometimes advantageous, because movement of additives between layers in the heat-developable light-sensitive material can be reduced.

The heat-developable light-sensitive materials according to the present invention are effective for forming negative images or positive images. Formation of the negative images or positive images will depend mainly upon selection of the specified light-sensitive silver halide. For example, in order to form direct positive images, it is possible to use inner image silver halide emulsions described in U.S. Pat. Nos. 2,592,250, 3,206,313, 3,367,778 and 3,447,927, or mixtures of a surface image silver halide emulsion described in U.S. Pat. No. 2,996,382 and an inner image silver halide emulsion.

A support used in the light-sensitive materials and dye fixing materials which are used, if necessary, in the present invention are those which resist processing temperature. As the general supports, there are not only glass, paper, metal and analogues thereof but also acetyl cellulose films, cellulose ester films, polyvinyl acetal films, polystyrene films, polycarbonate films, polyethylene terephthalate films and films which are related to these films, and resin materials. Further, paper supports laminated with a polymer such as polyethylene, etc., can be used. Polyesters described in U.S. Pat. Nos. 3,634,089 and 3,725,070 are suitably used.

In the pressent invention, various means for exposure can be used. Latent images are obtained by imagewise exposure of radiant rays containing visible light. Generally, light sources used for conventional color prints, for example, a tungsten lamp, a mercury lamp, a halogen lamp such as an iodine lamp, etc., a xenon lamp, a laser, and a CRT light source, fluorescent tubes and light emitting diodes, etc., can be used as light sources.

In the present invention, development is carried out by applying heat to the light-sensitive materials. The heating means may be a hot plate, iron, heat roller, exothermic materials utilizing carbon or titanium white, etc., or analogues thereof.

The transfer of dyes from the light-sensitive layer to the dye fixing layer can be carried out using a dye transfer assistant.

The dye transfer assistants suitably used in a process wherein it is supplied from the outside, include water and an alkaline aqueous solution containing sodium hydroxide, potassium hydroxide or an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant may be used by wetting the image receiving layer with the transfer assistant.

When the dye transfer assistant is incorporated into the light-sensitive material or the dye fixing material, it is not necessary to supply the transfer assistant from the outside. In this case, the above described dye transfer assistant may be incorporated into the material in the form of water of crystallization or microcapsules or as a precursor which releases a solvent at a high temperature.

A more preferred process is a process wherein a hydrophilic thermal solvent which is solid at an ambient temperature and melts at a high temperature is incorporated into the light-sensitive material or the dye fixing material. The hydrophilic thermal solvent can be incorporated either into any of the light-sensitive material and the dye fixing material or into both of them. Although the solvent can be incorporated into any of the emulsion layer, the intermediate layer, the protective layer and the dye fixing layer, it is preferred to incorporate it into the dye fixing layer and/or adjacent layers thereto.

Examples of the hydrophilic thermal solvents include areas, pyridines, amides, sulfonamides, imides, alcohols, oximes and other heterocyclic compounds.

In the present invention, imagewise distribution of mobile dyes corresponding to exposure is formed in the light-sensitive material by heat development, and processes of obtaining visible images by transferring the image dyes to a dye fixing material (the so-called diffusion transfer) have been described in the above described cited patents and Japanese Patent Application Nos. 42092/83 and 55172/83 (corresponding to U.S. Ser. No. 590,592 filed on Mar. 16, 1984).

In the light-sensitive materials of the present invention, mobile dyes can be imagewise formed by heating to about 80° to about 250° C. after exposing to light.

In order to make a visible image, mobile dyes are transferred to, for example, a dye fixing layer, and fixed therein. Then, the fixed layer is separated or an opaque layer is provided between the dye providing substance-containing layer and the dye fixing layer, whereby a color image can be watched from the reverse side.

The dye fixing layer desirably contains, for example, dye mordanting agents in order to fix the dyes.

The support having the light-sensitive layers and the support having the dye fixing layer may be identical or may be provided separately. In the case of providing separately, the material having the dye fixing layer is called a dye fixing material.

With respect to other compounds capable of being used in the light-sensitive materials in the present invention, for example, sulfamide derivatives, cationic compounds having a pyridinium group, etc., surfactants having a polyethylene oxide chain, antihalation and antiirradiation dyes, hardeners and mordanting agents, etc., it is possible to use those described in European Pat. Nos. 76,492 and 66,282, West German Pat. No. 3,315,485, and Japanaese Patent Application (OPI) Nos. 65839/84 and 152440/84.

Further, as methods of exposure, those cited in the above described patents can be used.

EXAMPLE 1

Preparation of Thermally Decomposable Organic Silver Salt (3) Emulsion 28 g of gelatin and 16.2 g of phenylpropiolic acid were dissolved in 3,000 ml of water. The resulting solution was stirred with keeping at 40° C. To the solution, a solution prepared by dissolving 17 g of silver nitrate in 100 ml of water was added over a 2 minute period. The pH of the resulting solution was controlled to cause precipitation, and excess salts were removed. Thereafter, the pH was adjusted to 6.0 to obtain a silver phenylpropiolate emulsion in a yield of 400 g.

Preparation of Silver Iodobromide Emulsion 40 g of gelatin and 26 g of KBr were dissolved in 3,000 ml of water. The resulting solution was stirred at 50° C. A solution prepared by dissolving 34 g of silver nitrate in 200 ml of water was then added to the above described solution over 10 minutes. Thereafter, a solution prepared by dissolving 3.3 g of KI in 100 ml of water was added over a 2 minute period. The pH of the resulting silver iodobromide emulsion was controlled to cause precipitation, and excess salts were removed. Thereafter, the pH was adjusted to 6.0 to obtain a silver iodobromide emulsion in a yield of 400 g.

A coating solution having the following composition was applied to a polyethylene terephthalate support so as to have a wet film thickness of 60 μm to produce Light-Sensitive Material (A).

Silver Iodobromide Emulsion: 10 g
Thermally Decomposable Organic Silver Salt (3) Emulsion: 30 g
Gelatin (10% aqueous solution): 10 g
Hydroquinone (5% aqueous solution): 15 ml
Polyethylene Glycol Type Surfactant (5% aqueous solution): 5 ml This light-sensitive material was exposed imagewise to light at 2,000 luxes for 5 seconds using a tungsten lamp. Thereafter, when it was heated uniformly on a heated block at 140° C. for 10 seconds, a brown image was obtained, the maximum density of which was 0.94 and the minimum density of which was 0.19. For comparison, the thermally decomposable organic silver salt (3) emulsion of the present invention was removed from the above described coating solution, and a coating solution prepared by adding a corresponding aqueous solution of gelatin was applied in a simular manner and dried to produce Light-Sensitive Material (B). When it was exposed to light and heated in a similar manner, an image having a maximum density of 0.27 and a minimum density of 0.12 was obtained. It was shown that the thermally decomposable organic silver salt (3) of the present invention produces an image having high density.

EXAMPLE 2

Thermally decomposable organic salt (3) prepared as follows was used instead of the thermally decomposable organic silver salt (3) emulsion prepared as described in Example 1. Another preparation of thermally decomposable organic silver salt (3):

7.4 g of phenylpropiolic acid was dissolved in 100 ml of a solvent composed of 50% by volume of methanol and 50% by volume of distilled water. On the other hand, a solution was prepared by dissolving 8.0 g of silver nitrate in 100 ml of distilled water and this was mixed with the solution of phenylpropiolic acid with stirring. After the pH was adjusted to 6.0, the formed white precipitates were filtered off to obtain silver phenylpropiolate (3).

A coating material having the following composition was applied to a polyethylene terephthalate support so as to have a wet film thickness of 60 μm, and dried to produce a light-sensitive material.

Silver Iodobromide Emulsion (as described in Example 1): 10 g
Thermally Decomposable Organic Silver Salt (3): 2 g
Gelatin (10% aqueous solution): 20 g
Hydroquinone (5% aqueous solution): 15 ml
Polyethylene Glycol Type Surfactant (5% aqueous solution): 5 ml
Distilled Water: 20 ml When it was exposed to light and heated in a similar manner to Example 1, a brown developed image having a maximum density of 0.89 and a minimum density of 0.21 was obrained. It is understood from this fact that a useful thermally decomposable organic silver salt is obtained by merely mixing a solution of a thermally decomposable organic acid with a solution of silver nitrate, followed by filtration.

EXAMPLE 3

The maximum density and minimum density of the images were obtained by the same procedure as in Example 2 except that the following thermally decomposable organic salts prepared in a similar manner to Example 2 were used. The tone of the images was all brown-grayish black.

TABLE I

| Thermally Decomposable Organic Salt | | Maximum Density | Minimum Density |
| --- | --- | --- | --- |
| (5) | 2.6 g | 0.95 | 0.18 |
| (6) | 2.6 g | 0.92 | 0.17 |
| (24) | 2.0 g | 0.86 | 0.15 |
| (26) | 2.6 g | 0.94 | 0.17 |
| (40) | 1.7 g | 1.02 | 0.15 |
| (45) | 3.5 g | 0.77 | 0.15 |
| (53) | 3.0 g | 0.79 | 0.16 |

It can be seen that the thermally decomposable organic silver salts of the present invention have high density and low fog.

EXAMPLE 4

A thermally decomposable organic silver salt (3) emulsion was prepared in the same manner as in Example 1. A light-sensitive material was produced using the same procedures as in Example 1, except that a silver iodobromide emulsion (as described in Example 1) to which 3 ml of a 0.04 wt% solution of a spectrally sensitizing dye represented by the following formula in methanol was previously added was used.

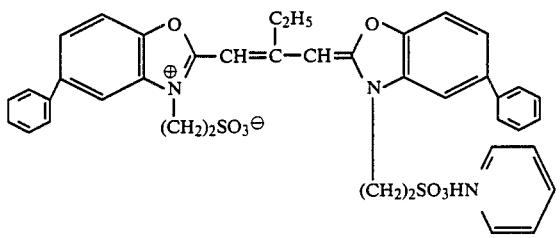

The light-sensitive material was imagewise exposed to light at 200 luxes for 5 seconds. Thereafter, when it was uniformly heated on a heated block at 140° C. for 10 seconds, an image having a maximum density of 0.99 and a minimum density of 0.21 was obtained. Moreover, the photographic sensitivity could be increased to about 2 times that of Example 1. This fact shows that photographic sensitivity is increased by addition of spectrally sensitizing dyes in using thermally decomposable organic silver salts of the present invention.

EXAMPLE 5

A light-sensitive material was produced using the same procedures as in Example 1, except that 15 ml of 4-hydroxymethyl-4-methyl-1-phenyl-3-pyrazolidone (10% solution in methanol) was used instead of hydroquinone (5% aqueous solution). When it was exposed to light and heated similarly, a brown image having a maximum density of 0.98 and a minimum density of 0.22 was obtained. This fact shows that the 3-pyrazolidone compound is effective as a developing agent.

EXAMPLE 6

Preparation of Thermally Decomposable Organic Silver Salt (40) Emulsion Containing Light-Sensitive Silver Bromide 6 g of 1,4-phenylene-bispropiolic acid and 10 g of gelatin were dissolved in 1,000 ml of water.

The resulting solution was stirred at 40° C.

Then, a solution prepared by dissolving 8.5 g of silver nitrate in 100 ml of water was added to the above described solution over a 2 minute period.

Then, a solution prepared by dissolving 1.2 g of potassium bromide in 50 ml of water was added thereto. The pH of the prepared emulsion was controlled to cause precipitation and excess salts were removed. Thereafter, the pH of the emulsion was adjusted to 6.0. The yield was 200 g.

A silver bromide emulsion containing silver benzotriazole was prepared in the same manner, except that 6.5 g of benzotriazole was used instead of 6 g of 1,4-phenylene-bispropiolic acid.

Preparation of Dispersion of Coupler in Gelatin 5 g of 2-dodecylcarbamoyl-1-naphthol, 0.5 g of sodium succinic acid-2-ethyl-hexyl ester sulfonate and 2.5 g of tricresyl phosphate (TCP) were weighed and dissolved by adding 30 ml of ethyl acetate. The resulting solution was mixed with 100 g of a 10% aqueous solution of gelatin with stirring and dispersed by a homogenizer at 10,000 rpm for 10 minutes.

A coating solution having the following composition was applied to a polyethylene terephthalate support so as to have a wet film thickness of 60 μm, and dried to produce Light-Sensitive Material (C).

(a) Thermally decomposable organic silver 10 g salt (40) emulsion containing light-sensitive silver bromide:
(b) Dispersion of coupler in gelatin: 3.5 g
(c) Solution prepared by dissolving 0.25 g of guanidinetrichloroacetic acid in 2.5 cc of ethanol:
(d) Gelatin (10% aqueous solution):
(e) Solution prepared by dissolving 0.2 g of 2,6-dichloro-p-aminophenol in 15 cc of water This light-sensitive material was exposed imagewise to light at 2,000 luxes for 5 seconds using a tungsten lamp. Thereafter, when it was heated uniformly on a heated block at 140° C. for 20 seconds, a negative cyan image was obtained. When the density of it was measured using a Macbeth transmission densitometer (TD-504), a minimum density of 0.28 and a maximum density of 2.10 was obtained. Then, the same coating solutions as that used in the Light-Sensitive Material (C), except that a silver bromide emulsion containing silver benzotriazole and 10 g of the following silver bromide emulsion were used, respectively, instead of the above described thermally decomposable organic silver salt (40) emulsion containing light-sensitive silver bromide, were prepared, and they were applied and dried to produce Light-Sensitive Materials (D) and (E), respectively.

Preparation of Silver Bromide Emulsion 10 g of gelatin and 7.2 g of KBr were dissolved in 1,000 ml of water. The resulting solution was stirred at 40° C. A solution prepared by dissolving 8.5 g of silver nitrate in 100 ml of water was then added to the above described solution over a 2 minute period. The prepared emulsion was precipitated by controlling the pH and excess salts were removed. Thereafter, the pH of the emulsion was adjusted to 6.0. The yield was 200 g.

When they were exposed to light and heated in a similar manner to Light-Sensitive Materil (C), the maximum density was 1.72 and the minimum density was 0.25 in Light-Sensitive Material (D) and the maximum density was 0.15 and the minimum density was 0.12 in Light-Sensitive Material (E).

It can be seen that thermally decomposable organic silver salts of the present invention are useful not only for black-and-white light-sensitive materials but also for heat-developable color light-sensitive materials in which dye images are obtained by coupling reactions. Further, it can be seen that they show a higher development rate than prior organic silver salts. Application of them to a system in which a diffusible dye is released by a coupling reaction is described in the following examples.

EXAMPLE 7

Preparation of Dispersion of Dye Providing Substance in Gelatin 10 g of a dye providing substance having the following structure:

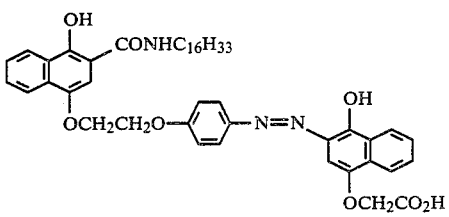

0.5 g of a surfactant: sodium succinic acid 2-ethylhexyl ester sulfonate and 4 g of tricresyl phosphate (TCP) were weighed, and 20 ml of cyclohexane was added thereto. They were dissolved with heating to obtain a uniform solution. After the resulting solution was mixed with 100 g of a 10% solution of lime-processed gelatin, it was dispersed using a homogenizer at 10,000 rpm for 10 minutes.

Then, a light-sensitive coating solution was prepared.
(a) Thermally decomposable organic silver salt (40) emulsion containing light-sensitive silver bromide (as described in Example 7): 10 g
(b) Dispersion of dye providing substance: 3.5 g
(c) Guanidinetrichloroacetic acid (10% solution in ethanol): 2.5 ml
(d) Gelatin (10% aqueous solution): 5 g
(e) Solution prepared by dissolving 200 ml of 2,6-dichloro-4-aminophenol in 2 ml of methanol.

After the above described (a) to (e) were blended to dissolve, the mixture was applied to a polyethylene terephthalate film so as to have a wet film thickness of 30 μm and dried. Then, the following composition was applied as a protective layer to the resulting layer so as to have a wet film thickness of 25 μm, and dried. The resulting light-sensitive material was designated (F).
(a) 10% aqueous solution of gelatin: 35 g
(b) 1% aqueous solution of sodium succinic acid-2-ethylhexyl ester sulfonate: 4 ml
(c) Guanidine trichloroacetic acid (10% ethanol): 4 ml
(d) Distilled water: 57 ml A coating solution having the same composition as described above, excpet that 10 g of a light-sensitive silver bromide emulsion described in Example 7 was used instead of the thermally decomposable organic silver salt (40) emulsion containing light-sensitive silver bromide, was prepared, and it was applied and dried to produce a Light-Sensitive Material (G).

Production of Dye Fixing Material 10 g of poly(methyl acetate-co-N,N,N-trimethyl-N-vinylbenzylammonium chloride) (molar ratio of methyl acrylate to vinylbenzylammonium chloride was 1:1) was dissolved in 200 ml of a 1.5% aqueous solution of sodium carbonate and uniformly mixed with 100 g of 10% lime-processed gelatin. The mixture was applied uniformly to a paper support laminated with polyethylene containing dispersed titanium oxide so as to have a wet film thickness of 90 μm, and dried. The resulting sample was used as a dye fixing material having a mordanting layer.

The above described Light-Sensitive Materials (F) and (G) were exposed imagewise to lgiht at 2,000 luxes for 10 seconds using a tungsten lamp. Thereafter, they were uniformly heated for 20 seconds on a heated block heated to 150° C. After the dye fixing material was immersed in water, it was put on the above described heated light-sensitive material so that the film face was in contact with it. After heating on a heated block at 80° C. for 6 seconds, the dye fixing material was separated from the light-sensitive material, by which a negative magenta dye was obtained on the image receiving material. When the density of the resulting negative images were measured using a Macbeth reflection densitometer (RD-519), an image having a maximum density of 2.15 and a minimum density of 0.26 was observed in Light-Sensitive Material (F), but an image having a maximum density of 0.16 was only observed in Light-Sensitive Material (G).

EXAMPLE 8

Preparation of Dispersion of Dye Providing Substance in Gelatin

To a mixture of 5 g of a reducible dye releasing agent having the following structure:

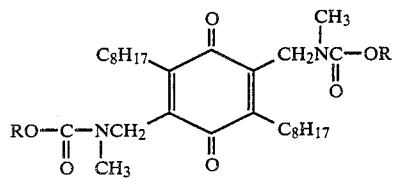

(wherein R represents a group having the following structure:

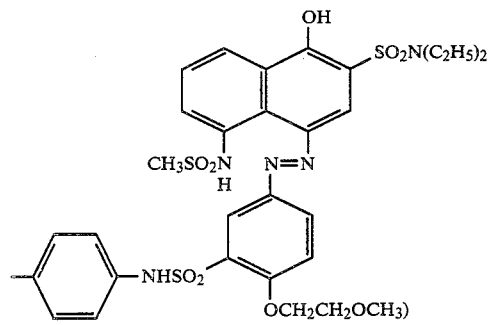

4 g of an electron donative substance having the following structure:

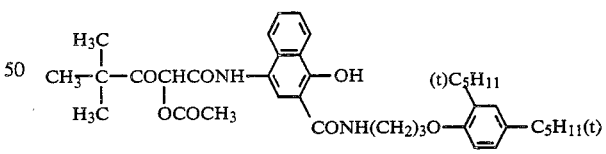

0.5 g of sodium succinic acid-2-ethylhexyl ester sulfonate and 10 g of tricresyl phosphate (TCP), 20 ml of cyclohexanone was added, and the mixture was dissolved with heating to about 60° C. After the resulting solution was mixed with 100 g of a 10% solution of gelatin with stirring, it was dispersed using a homogenizer at 10,000 rpm for 10 minutes.

Then, a light-sensitive coating solution was prepared.
(a) Thermally decomposable organic silver salt (40) emulsion containing light-sensitive silver bromide (as described in Example 7): 10 g
(b) Dispersion of dye providing substance: 3.5 g
(c) Solution prepared by dissolving 250 mg of guanidine trichloroacetic acid in 2 ml of ethanol:

(d) 5% aqueous solution of the following compound:

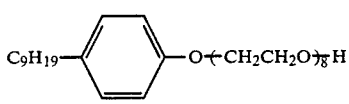

1.5 ml

To the above described mixture of (a) to (d), 2 ml of water was added and mixed. After dissolving with heating, it was applied to a polyethylene terephthalate film so as to have a wet film thickness of 30 μm, and dried to produce Light-Sensitive Material (H).

Further, a coating solution having the same composition as described above, except that 10 g of a light-sensitive silver bromide emulsion described in Example 7 was used instead of the thermally decomposable organic silver salt (40) emulsion containing light-sensitive silver bromide, was prepared, and it was applied and dried to produce Light-Sensitive Material (I).

Light-Sensitive Material (H) and (I) were exposed imagewise to light at 2,000 luxes for 10 seconds using a tungsten lamp. Thereafter, they were uniformly heated on a heated block heated to 130° C. for 3 seconds After the dye fixing material described in Example 8 was immersed in water, it was put on the above described heated light-sensitive material so that the film face was in contact with it. A positive magenta image was obtained on the dye fixing material. When the density of the positive images was measured using a Macbeth reflection densitometer (RD-519), Light-Sensitive Material (H) showed a maximum density of 1.82 and a minimum density of 0.31 as densities to green light, but Light-Sensitive Material (I) showed a maximum density of 1.90.

EXAMPLE 9

Preparation of Silver Iodobromide 40 g of gelatin and 26 g of KBr were dissolved in 3,000 ml of water. The resulting solution was stirred at 50° C. Then, a solution prepared by dissolving 34 g of silver nitrate in 200 ml of water was added to the above described solution over a 10 minute period.

Thereafter, a solution prepared by dissolving 3.3 g of KI in 100 ml of water was added thereto over 2 minutes. The pH of the resulting silver iodobromide emulsion was controlled to cause precipitation, and excess salts were removed.

Thereafter, the pH was adjusted to 6.0, by which a silver iodobromide emulsion was obtained in a yield of 400 g.

Preparation of Thermally Decomposable Organic Silver Salt (40) Emulsion 28 g of gelatin and 11.9 g of 1,4-phenylenebispropiolic acid were dissolved in 3,000 ml of water. The resulting solution was stirred at 40° C. To this solution, a solution prepared by dissolving 17 g of silver nitrate in 100 ml of water was added over 2 minutes. The pH of the mixed solution was controlled to cause precipitation, and excess salts were removed. Thereafter, the pH was adjusted to 6.0 to obtain a thermally decomposable organic silver salt (40) emulsion in a yield of 400 g.

Preparation of a Dispersion of a Dye Providing Substance in Gelatin 5 g of a magenta dye providing substance (2), 0.5 g of sodium succinic acid 2-ethyl-hexyl ester sulfonate and 5 g of tricresyl phosphate (TCP) were weighted, and 30 ml of ethyl acetate was added thereto. The mixture was dissolved with heating to about 60° C. to produce a uniform solution. After this solution was mixed with 100 g of a 10% solution of gelatin with stirring, it was dispersed by a homogenizer at 10,000 rpm for 10 minutes.

This dispersion is called dispersion of dye providing substance (2).

Preparation of Light-Sensitive Materials (J), (K) and (L): Light-Sensitive Material (J)

(a) The above described silver halide emulsion: 25 g
(b) Dispersion of dye providing substance (2): 33 g
(c) 5% aqueous solution of a compound having the following structure:

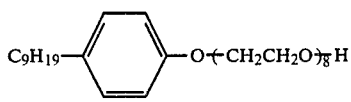

10 ml
(d) 10% solution of dimethylsulfamide in ethanol: 4 ml
(e) Guanidine trichloroacetic acid (10% solution in ethanol): 15 ml The above described (a) to (e) were mixed. After being dissolved, the mixture was applied to a polyethylene terephthalate film so as to have a wet film thickness of 30 μm, and dried. Further, the following composition was applied as a protective layer to the resulting layer so as to have a wet film thickness of 25 μm, and dried.

(a) 10% aqueous solution of gelatin: 35 g
(b) 1% aqueous solution of sodium succinic acid-2-ethylhexyl ester sulfonate: 4 ml
(c) Water: 61 ml Light-Sensitive Material (K)

(a) Thermally decomposable organic silver salt (40) emulsion: 10 g
(b) Silver iodobromide emulsion: 20 g
(c) Dispersion of dye providing substance (2): 33 g
(d) 5% aqueous solution of the compound having the following structure:

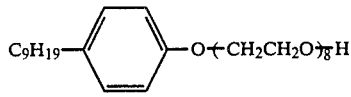

10 ml
(e) 10% solution of dimethylsulfamide in ethanol: 4 ml
(f) Guanidine trichloroacetic acid (10% solution in ethanol): 16 ml After the above described (a) to (f) were mixed to dissolve, the mixture was applied to a polyethylene terephthalate film so as to have a wet film thickness of 30 μm, and dried. Further, the same composition as in Light-Sensitive Material (J) was applied as a protective layer to the resulting layer so as to have a wet film thickness of 25 μm, and dried.

Preparation of Dye Fixing Material 10 g of poly(methyl acrylate-co-N,N,N-trimethyl-N-vinylbenzylammonium chloride) (molar ratio of methyl acrylate to vinylbenzylammonium chloride was 1:1) was dissolved in 200 ml of water, and uniformly mixed with 100 g of 10% lime-processed gelatin. The resulting mixture was applied to a paper support laminated with polyethylene containing titanium dioxide so as to have a wet film thickness of 90 μm. After the resulting sample was dried, it was used as a dye fixing material.

The above described Light-Sensitive Materials (J), (K) and (L) were imagewise exposed to light at 2,000 luxes for 10 seconds using a tungsten lamp. They were then uniformly heated on a heated block heated to 140° C.

After the film face of the dye fixing material was immersed in water, each of the above described Light-Sensitive Materials (J), (K) and (L) was put on the fixing material so as to be in contact with the film face, and it was uniformly heated for 6 seconds on a heated block heated to 80° C. When the dye fixing material was separated from the light-sensitive material, a negative magenta image was obtained on the fixing material.

Light-Sensitive Material (L)

Light-Sensitive Material (L) was produced by the same manner as in Light-Sensitive Material (K), except that 10 g of a silver benzotriazole emulsion prepared as follows was used instead of the thermally decomposable organic silver salt (40) emulsion in Light-Sensitive Material (K).

Preparation of Silver Benzotriazole Emulsion 28 g of gelatin and 13.2 g of benzotriazole were dissolved in 3,000 ml of water. The resultant solution was stirred with keeping at 40° C. To this solution, a solution prepared by dissolving 17 g of silver nitrate in 100 ml of water was added over 2 minutes. The pH of the resulting silver benzotriazole emulsion was controlled to cause precipitation, and excess salts were removed. Thereafter, the pH was adjusted to 6.0 to obtain a silver benzotriazole emulsion in a yield of 400 g.

When the density of the resulting negative images was measured using a Macbeth reflection densitometer (RD-519), the following results were obtained.

| Sample No. | Maximum Density | Minimum Density |
|---|---|---|
| (J) (Comparison) | 1.43 | 0.13 |
| (K) (The present invention) | 2.14 | 0.20 |
| (L) (Comparison) | 1.76 | 0.18 |

It is understood from the above described results that the thermally decomposable organic silver salt (40) of the present invention gives high maximum density and low minimum density.

EXAMPLE 10

Thermally decomposable organic silver salt (40) prepared as follows was used instead of the theramlly decomposable organic silver salt (40) emulsion in Example 9.

5.5 g of phenyl-1,4-dipropiolic acid was dissolved in 100 ml of a solvent composed of 50% by volume of methanol and 50% by volume of water. On the other hand, a solution was prepared by dissolving 8.0 g of silver nitrate in 100 ml of water, and it was mixed with the solution of 1,4-phenylene bispropiolic acid with stirring. After the pH was adjusted to 6.0, the formed yellowish white precipitates were filtered off to obtain silver 1,4-phenylene-bispropiolate (40).

A coating material having the following composition was applied to a polyethylene terephthalate support so as to have a wet film thickness of 30 μm, and dried.
(a) Thermally decomposable organic silver salt (40) emulsion: 0.6 g
(b) Silver iodobromide emulsion (as described in Example 9): 20 g
(c) Dispersion of dye providing substance (2) (as described in Example 9): 33 g
(d) 5% aqueous solution of the compound having the following structure:

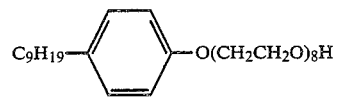

10 ml
(e) Dimethylsulfamide (10% solution in ethanol): 4 ml
(f) Guanidine trichloroacetic acid (10% sulution in ethanol): 16 ml
(g) Gelatin (3.5% aqueous solution): 10 g Further, a protective layer described in Example 9 was applied to the resulting layer so as to have a wet film thickness of 25 μm, and dried to produce a light-sensitive material.

When it was processed by the same manner as in Example 9, a negative magenta image having a maximum density of 2.07 and a minimum density of 0.29 was obtained on the fixing material. It is understood from this result that a useful thermally decomposable organic silver salt is obtained by merely mixing a solution of the thermally decomposable organic acid with a solution of silver nitrate, followed by filtration.

EXAMPLE 11

Maximum density and minimum density of images obtained by the same procedures as in Example 10, except that the following thermally decomposable organic silver salts prepared by the same manner as in Example 10 were used, are shown in Table II.

TABLE II

| Thermally Decomposable Organic Silver Salt | | Maximum Density | Minimum Density |
|---|---|---|---|
| (3) | 0.7 g | 1.98 | 0.30 |
| (5) | 0.9 g | 2.03 | 0.26 |
| (6) | 0.9 g | 2.00 | 0.22 |
| (24) | 0.7 g | 1.81 | 0.18 |
| (26) | 0.9 g | 1.86 | 0.18 |
| (45) | 1.2 g | 1.61 | 0.14 |
| (53) | 1.0 g | 1.55 | 0.14 |

It is understood that the thermally decomposable organic silver salts of the present invention show high density and low fog.

EXAMPLE 12

Dispersions of dye providing substance were produced by the same procedures as in Example 9, except that the following dye providing substances were used instead of the dye providing substance (2) of Example 9.

Dye providing substance (8): 5 g Dispersion (I)
Dye providing substance (4): 7.5 g Dispersion (II)
Dye providing substance (12): 5 g Dispersion (III)

Samples were produced by the same procedures as in Example 9 and processed by the same manner as in Example 9. The results obtained are shown below.

| Dispersion of Dye Providing Substance | Maximum Density | Minimum Density |
|---|---|---|
| Dispersion (I) (Magenta) | 2.14 | 0.16 |
| Dispersion (II) (Yellow) | 1.89 | 0.18 |
| Dispersion (III) (Cyan) | 2.25 | 0.23 |

It is understood from the above described results that the thermally decomposable organic silver salts of the present invention are effective for all dye providing substances.

EXAMPLE 13

Preparation of a Thermally Decomposable Organic Silver Salt (40) Emulsion Containing Light-Sensitive Silver Bromide 6 g of 1,4-phenylene-bispropiolic acid and 10 g of gelatin were dissolved in 1,000 ml of water. The resulting solution was stirred with keeping at 40° C.

Then, a solution prepared by dissolving 8.5 g of silver nitrate in 100 ml of water was added to the above described solution over 2 minutes.

Then, a solution prepared by dissolving 1.2 g of potassium bromide in 50 ml of water was added thereto over 2 minutes.

The prepared emulsion was subjected to controlling pH to cause precipitation, and excess salts were removed. Thereafter, the pH of the emulsion was adjusted to 6.0. The yield was 200 g.

Preparation of Light-Sensitive Material (M)

(a) Thermally decomposable organic silver salt (40) emulsion containing light-sensitive silver bromide: 25 g
(b) Dispersion of dye providing substance (2) (as described in Example 9): 33 g
(c) 5% aqueous solution of the compound having the following structure:

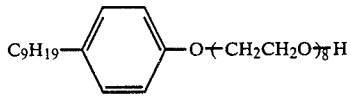

10 ml (d) Dimethylsulfonamide (10% solution in ethanol): 4 ml
(e) Guanidine trichloroacetic acid (10% solution in ethanol): 15 ml After the above described (a) to (e) were mixed to dissolve, the mixture was applied to a polyethylene terephthalate film so as to have a wet film thickness of 30 μm, and dried. Further, a protective layer having a composition described in Example 9 was applied to the resultant layer so as to have a wet film thickness of 25 μm, and dried.

The same coating solution as described above, except that 25 g of the following light-sensitive silver bromide emulsion was used instead of the thermally decomposable organic silver salt (40) emulsion containing light-sensitive silver bromide, was prepared, and it was applied and dried to produce Light-Sensitive Material (N).

Preparation of Silver Bromide Emulsion 10 g of gelatin and 7.2 g of KBr were dissolved in 1,000 ml of water. The resulting solution was stirred with keeping at 40° C. Then, a solution prepared by dissolving 8.5 g of silver nitrate in 100 ml of water was added to the above described solution over 2 minutes. The prepared emulsion was subjected to controlling of pH to cause precipitation, and excess salts were removed. Thereafter, the pH of the emulsion was adjusted to 6.0. Yield was 200 g.

When Light-Sensitive Materials (M) and (N) were processed in a similar manner to Example 9, the following magenta images were obtained.

| Sample No. | Maximum Density | Minimum Density |
|---|---|---|
| (M) (The present invention) | 1.83 | 0.14 |
| (N) (Comparison) | 0.18 | 0.12 |

It is understood that the thermally decomposable organic silver salt of the present invention is effective even in the case of preparing in the same system of light-sensitive silver halide.

While the invention has been described in detail and with reference to specific embodiments thereof, it will be apparent to one skilled in the art that various changes and modifications can be made therein without departing from the spirit and scope thereof.

What is claimed is:

1. A heat-developable light-sensitive material comprising, on a support,
   (a) a light-sensitive silver halide,
   (b) a thermally decomposable organic silver salt,
   (c) a binder, and
   (d) a reducing agent,
   wherein said thermally decomposable organic silver salt is represented by general formula (II):

wherein $R^0$ represents a monovalent residue selected from the group consisting of a hydrogen atom, an alkyl group, a substituted alkyl group, a cycloalkyl group, an alkenyl group, an alkynyl group, an aryl group, a substituted aryl group, a heterocyclic residue, a substituted heterocyclic residue, an aralkyl group, a substituted aralkyl group, an acyl group, an alkoxycarbonyl group, a carbamoyl group, a substituted carbamoyl group, —$CO_2M$ (wherein M represents an alkali metal) and —$CO_2B$, or a divalent residue selected from the group consisting of an alkylene group, an arylene group and a heterocyclic divalent residue, wherein B is a conjugated acid of an organic base or a quaternary ammonium group and m represents an integer of 1 to 4.

2. The heat-developable light-sensitive material as claimed in claim 1, wherein said reducing agent is a dye providing substance which is reductive and is oxidized to image release a mobile dye when heated.

3. The heat-developable light-sensitive material as claimed in claim 1, wherein said light-sensitive silver halide is selected from the group consisting of silver chloride, silver chlorobromide, silver chloroiodide, silver bromide, silver iodobromide, silver chloroiodobromide and silver iodide.

4. The heat-developable light-sensitive material as claimed in claim 3, wherein said light-sensitive silver halide has an average particle size of 0.001 μm to 10 μm.

5. The heat-developable light-sensitive material as claimed in claim 4, wherein said light-sensitive silver halide has an average particle size of 0.001 μm to 5 μm.

6. The heat-developable light-sensitive material as claimed in claim 1, wherein said light-sensitive silver halide is employed in an amount of from 1 mg/m² to 10 g/m².

7. The heat-developable light-sensitive material as claimed in claim 1, wherein said thermally decomposable organic silver salt is a silver salt of a carboxylic acid which undergoes decarboxylation at 80° C. to 250° C.

8. The heat-developable light-sensitive material as claimed in claim 7, wherein said thermally decomposable organic silver salt is a silver salt of carboxylic acid which undergoes decarboxylation at 100° C. to 200° C.

9. The heat-developable light-sensitive material as claimed in claim 1, wherein said thermally decomposable organic silver salt is coated in an amount of 10 mg/m² to 10 g/m² as silver.

10. The heat-developable light-sensitive material as claimed in claim 1, wherein said binder is a hydrophilic binder selected from the group consisting of a protein derivative, a cellulose derivative, a polysaccharide and a synthetic polymer.

11. The heat-developable light-sensitive material as claimed in claim 2, wherein said dye providing substance is represented by general formula (IV): $R_a$—SO$_2$—D, wherein $R_a$ represents a reducing group and D represents an image forming dye moiety containing a hydrophilic group.

12. The heat-developable light-sensitive material as claimed in claim 1, wherein said reducing agent is selected from the group consisting of a hydroquinone, an aminophenol, a catechol, a phenylenediamine and a 3-pyrazolidone.

13. The heat-developable light-sensitive material as claimed in claim 12, wherein said 3-pyrazolidone is selected from the group consisting of 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone and 5-methyl-3-pyrazolidone.

14. The heat-developable light-sensitive material as claimed in claim 1, wherein said reducing agent is employed in an amount of from 0.1 mol to 20 mols per mol of silver.

15. The heat-developable light-sensitive material as claimed in claim 14, wherein said reducing agent is employed in an amount of from 0.1 mol to 10 mols per mol of silver.

16. The heat-developable light-sensitive material as claimed in claim 11, wherein said $R_a$ is represented by formulae (V) to (XII)

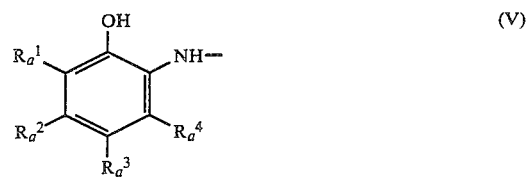

(V)

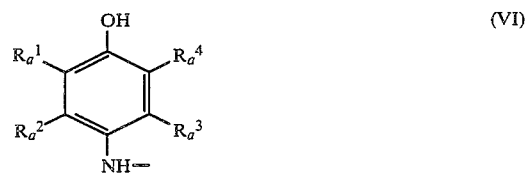

(VI)

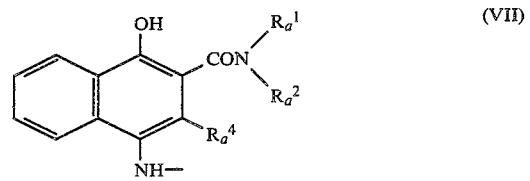

(VII)

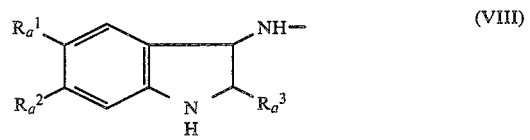

(VIII)

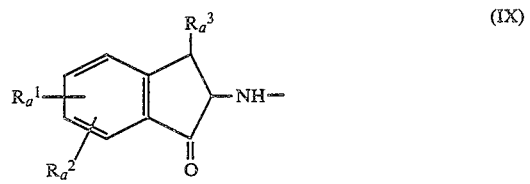

(IX)

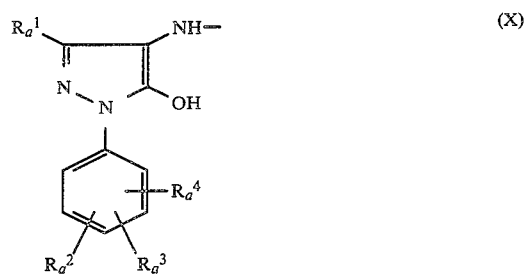

(X)

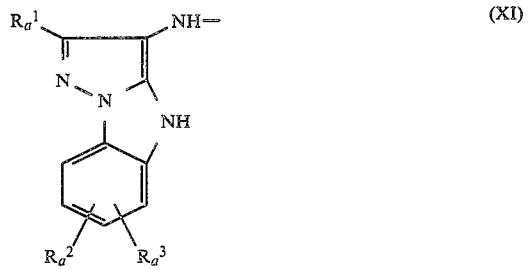

(XI)

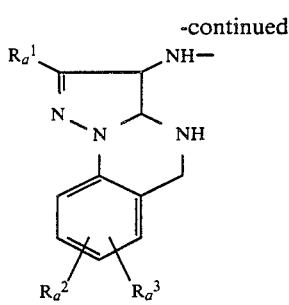

(XII)

wherein $R_a^1$, $R_a^2$, $R_a^3$ and $R_a^4$ each represents a hydrogen atom or a substituent selected from an alkyl group, a cycloalkyl group, an aryl group, an alkoxy group, an aryloxy group, an arylkyl group, an acyl group, an acylamino group, an alkylsulfonylamino group, an arylsulfonylamino group, an aryloxyalkyl group, an alkoxyalkyl group, an N-substituted carbamoyl group, an N-substituted sulfamoyl group, a halogen atom, an alkylthio group or an arylthio group.

* * * * *